United States Patent [19]
Kitaoka

[11] Patent Number: 6,127,690
[45] Date of Patent: Oct. 3, 2000

[54] ULTRAVIOLET AND VISIBLE LIGHT ABSORBANCE DETECTOR

[75] Inventor: Mitsuo Kitaoka, Kyoto, Japan

[73] Assignee: Shimadzu Corporation, Kyoto, Japan

[21] Appl. No.: 09/207,479

[22] Filed: Dec. 8, 1998

[30] Foreign Application Priority Data

Dec. 10, 1997 [JP] Japan ................................ 9-362266

[51] Int. Cl.⁷ .................................................. G01N 15/06
[52] U.S. Cl. ....................... 250/573; 250/576; 356/246; 73/61.48
[58] Field of Search ..................................... 250/573, 574, 250/575, 576, 216; 356/410, 411, 440, 246; 73/61.48, 61.69

[56] References Cited

U.S. PATENT DOCUMENTS 5,398,110  3/1995  Kitaoka .................................. 356/130

*Primary Examiner*—Seungsook Ham
*Assistant Examiner*—Kevin Pyo
*Attorney, Agent, or Firm*—Majestic, Parsons, Siebert & Hsue P.C.

[57] ABSTRACT

An ultraviolet and visible light absorbance detector uses a flow cell having a sample cell opening and a reference opening formed therethrough extending parallel to each other. The reference opening has a cross-sectional shape which is elongated in a direction perpendicular to the direction of its extension. An optical system causes an image of a slit to be formed with dispersed light over an area which includes light-receiving windows of both these openings, and portions of the dispersed light, after passing through these openings, are individually detected by light-receiving elements of a light-receiving device. Since the reference opening has an increased sectional area and its light throughput is increased, the absorbance noise due to the reference opening is reduced and the overall S/N ratio of the detector is improved.

12 Claims, 3 Drawing Sheets

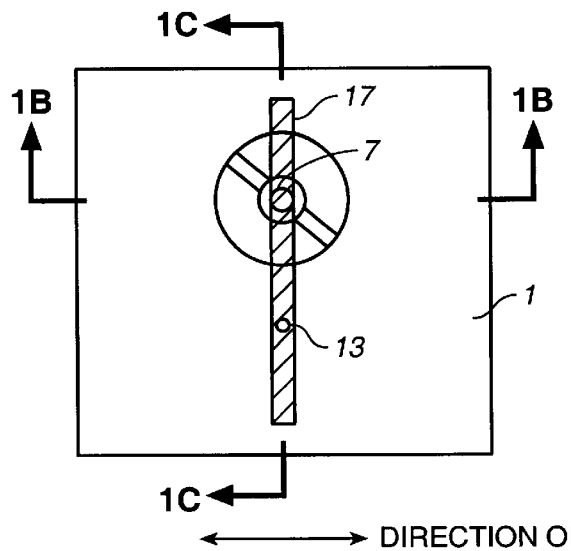
FIG._1A
*(PRIOR ART)*
← DIRECTION OF DISPERSION →
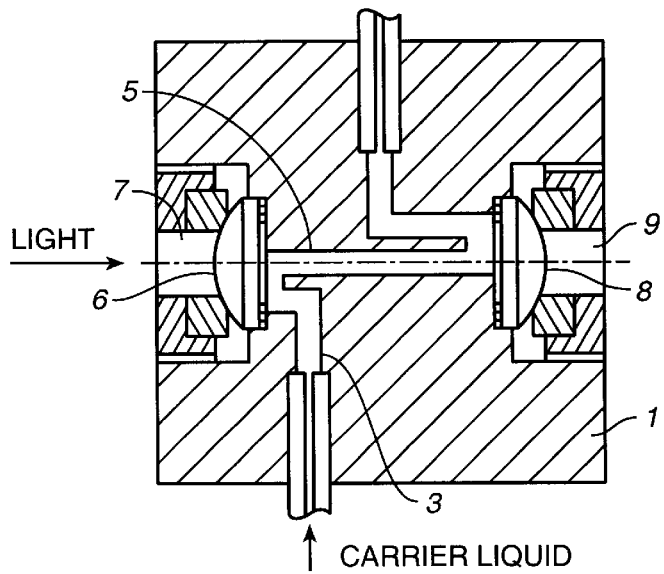
FIG._1B
*(PRIOR ART)*
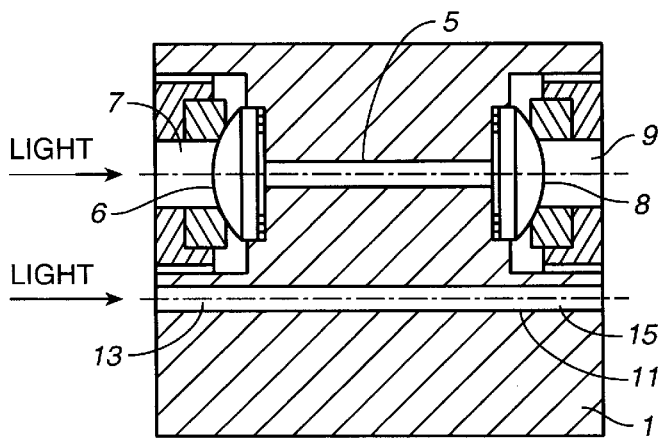
FIG._1C
*(PRIOR ART)*

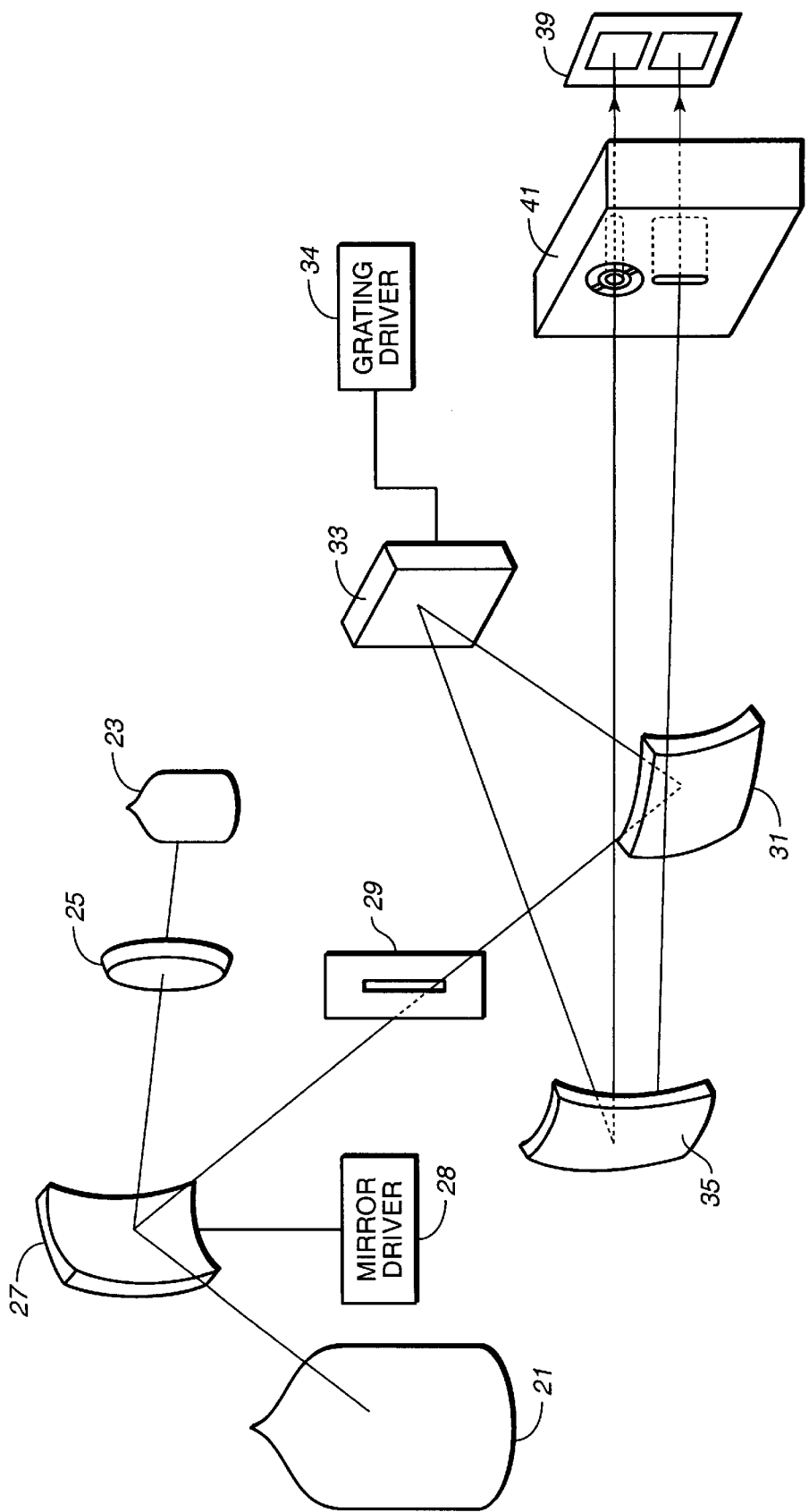
FIG._2

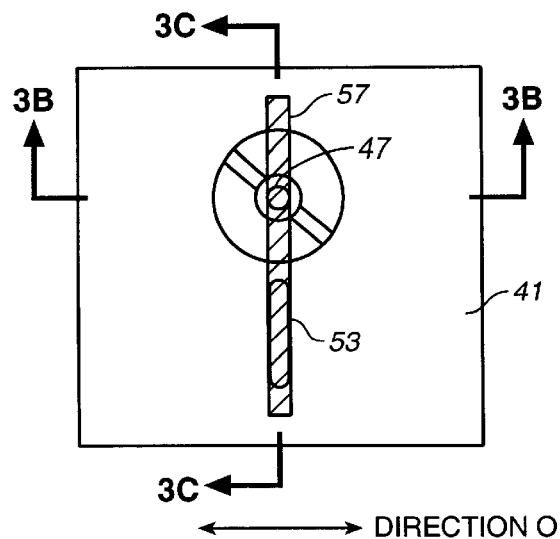
FIG._3A
DIRECTION OF DISPERSION
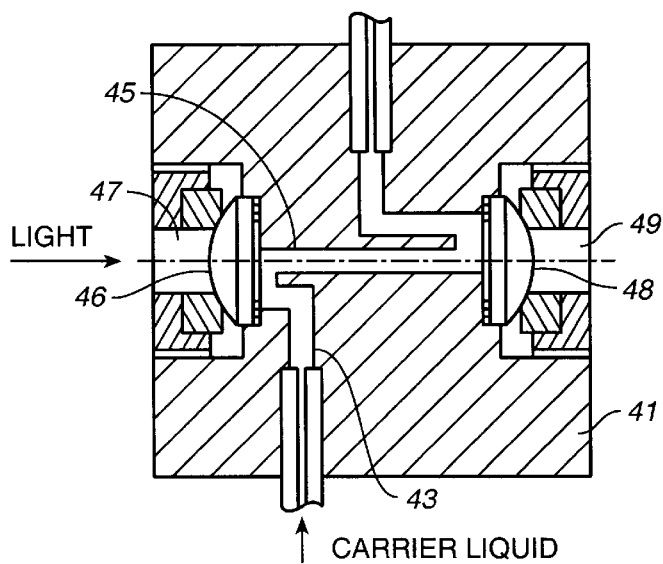
FIG._3B
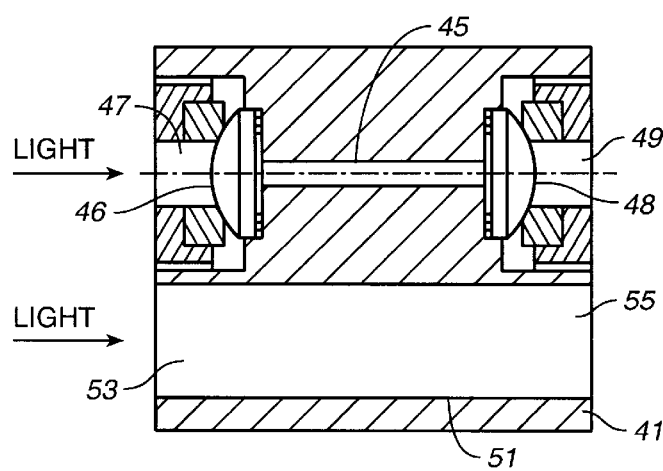
FIG._3C

ULTRAVIOLET AND VISIBLE LIGHT ABSORBANCE DETECTOR

BACKGROUND OF THE INVENTION

This invention relates to a spectrophotometer and more particularly to an ultraviolet and visible light absorbance detector of a kind provided with a flow cell having an elongated sample cell opening and a reference opening parallel thereto. Such a spectrophotometer is frequently used in high-power liquid chromatography.

When components of a sample contained in a carrier liquid are to be analyzed by measuring their ultraviolet and visible light absorbance, it has been known to use a detector of the kind described above. The optical system of such a detector of the so-called variable wavelength type may be formed so as to direct a beam of light from a source such as a $D_2$ lamp or tungsten lamp to a grating by means of mirrors and through a slit with a rectangular opening and to form an image of the slit with the light dispersed by the grating on an area of the flow cell covering the light-receiving windows of both the sample cell opening and the reference opening.

FIGS. 1A, 1B and 1C show an example of such a prior art flow cell 1, having a Z-shaped zigzagging carrier liquid flow route 3 therethrough. A portion of this Z-shaped carrier liquid flow route 3, indicated by numeral 5, serving as what was referred to as "the sample cell opening" above, is formed so as to be parallel to the optical path of the dispersed light made incident onto the flow cell 1. The length of the light path through the sample cell opening 5 may be about 10 mm, its inner diameter being about 1 mm. A portion of the dispersed light guided to the flow cell 1 passes through a converging lens 6, enters the sample cell opening 5 through its light-receiving window 7 on the incident side, traverses the sample cell opening 5, passes through another converging lens 8 and is projected out through a light-emitting window 9. As shown in FIG. 1C, the flow cell 1 is also provided with a reference opening 11 with inner diameter 1 mm, extending parallel to the sample cell opening 5. Another portion of the dispersed light guided to the flow cell 1 is introduced into the reference opening 11 through its light-receiving window 13 and is emitted out through its light-emitting window 15.

The image of the slit formed on the flow cell 1 by the optical system is elongated in the direction perpendicular to the direction of the spectral dispersion (as indicated by numeral 17 in FIG. 1A). The sample cell opening 5 and the reference opening 11 are arranged such that the image 17 covers both the light-receiving windows 7 and 13 of both the sample cell opening 5 and the reference opening 11.

The portions of light which pass through the sample cell opening 5 and the reference opening 11 are each detected by a separate detector such as a photodiode. The intensity thus detected is used to calculate absorbance ("absorbance conversion") from which target components in the sample are detected.

With a detector of the kind described above, it is very important to improve its S/N ratio. One method of doing so is to increase the signal intensity, but the length and the inner diameter of the sample cell opening cannot be increased indiscriminately because the detected separate chromatographic peaks should not be overly broadened and the sensitivity of the detector should be kept high. In other words, it is not feasible to increase the signal intensity.

The S/N ratio can be increased also by reducing the noise (N). In order to reduce the noise, it may be suggested that the throughput of light inside the sample cell should be increased, but the inner diameter of the sample cell opening is not to be increased beyond about 1 mm because the monochromatic characteristic of the incident light should be maintained. In other words, its throughput is uniquely determined and cannot be hoped to be increased. In summary, it is not an easy task to reduce the absorption noise caused by the sample cell opening.

SUMMARY OF THE INVENTION

It is therefore an object of this invention to improve the S/N ratio of an absorbance detector by reducing the noise caused by the light passing through the reference opening.

Since both portions of the light passing through the sample cell opening and the reference opening contribute to the overall noise of the detector, the noise of the detector as a whole can be reduced and its S/N ratio can be improved even if only the noise in absorbance caused by the reference opening is reduced. If the inner diameter of the reference opening is increased for this purpose, however, the monochromatic characteristic of the light is adversely affected, although the light throughput is increased. Moreover, the variations in the conditions of light passing through these two openings may not cancel each other as completely, and the stability of the base line may also be adversely affected. In summary, it was not a practical solution to the problem to increase the inner diameter of the reference opening indiscriminately.

A detector embodying this invention, with which the above and other objects can be accomplished, may be characterized not only as comprising a flow cell having a sample cell opening and a reference opening formed therethrough extending parallel to each other, an optical system for forming an image of a slit with dispersed light over an area which covers light-receiving windows of both these openings and causing this monochromatic focused light to pass through these openings, and a light-receiving device for individually detecting the portions of the light which have passed through these two openings each with a light-receiving element, but also wherein the reference opening is cross-sectionally elongated in a direction perpendicular to the direction of its extension.

With a detector thus formed, the light throughput is increased because the sectional area of the reference opening is large. Thus, the absorbance noise due to the reference opening is reduced and the overall S/N of the detector is improved. Since only dispersed light is made incident into the reference opening, the monochromatic characteristic of the light passing through the reference opening is not adversely affected.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1A is a front view of a prior art flow cell, FIG. 1B is its sectional plan view taken along line 1B—1B of FIG. 1A, and FIG. 1C is its sectional side view taken along line 1C—1C of FIG. 1A;

FIG. 2 is a schematic structural diagram of an ultraviolet and visible light absorbance detector embodying this invention; and FIG. 3A is a front view of the flow cell of FIG. 2, FIG. 3B is its sectional plan view taken along line 3B—3B of FIG.

3A, and FIG. 3C is its sectional side view taken along line 3C—3C of FIG. 3A.

DETAILED DESCRIPTION OF THE INVENTION

The invention is described next by way of an example with reference to FIGS. 2, 3A, 3B and 3C but this example is not intended to limit the scope of the invention.

As schematically shown in FIG. 2, a $D_2$ lamp 21 and a tungsten lamp 23 are both used as a light source, and a filter 25 is provided on the light path of the tungsten lamp 23. Not only is a mirror 27 disposed at the common point on the light paths of both the $D_2$ lamp 21 and the tungsten lamp 23, but also a mirror driver 28 is provided for rotating the mirror 27 strategically such that either of these two lamps 21 and 23 can be selected as the light source of the detector.

A slit 29 with a rectangular opening is provided on the path of the light reflected by the mirror 27 so as to provide a beam of light with a rectangular cross-sectional shape. Another mirror 31 is disposed on the path of the light from the slit 29, and a grating 33 for dispersing the light emitted from the light source is disposed on the path of the reflected light from this mirror 31. The grating 33 is provided with its own driver 34 serving to rotate the grating 33 so as to direct the dispersed light therefrom to still another mirror 35 which is disposed and oriented such that the dispersed light reflected thereby is directed to a flow cell 41. On the rear side of the flow cell 41 opposite from its light incident side, there is disposed a light-receiving device 39 for detecting the light passing through the sample cell opening and the reference opening of the flow cell 41 (to be described in detail below) by means of respective light-receiving elements.

As shown more in detail in FIGS. 3A, 3B and 3C, the flow cell 41 embodying this invention may comprise a stainless steel block having a generally Z-shaped zigzagging carrier liquid flow route 43 formed therethrough. A portion of this Z-shaped carrier liquid flow route 43 is parallel to the path of the dispersed light made incident onto the flow cell 41, serving as the sample cell opening (indicated by numeral 45) with optical path length of the light traveling therethrough equal to about 10 mm and inner diameter 1 mm, for example.

A portion of the dispersed light made incident onto the flow cell 41 enters the sample cell opening 45 from its light-receiving window 47 through a converging lens 46, leaving from its light-emitting window 49 through another converging lens 48. The flow cell 41 is also provided with a reference opening 51 formed therethrough parallel to the sample cell opening 45, say, by a so-called wire-cut discharge process. The reference opening 51 has an elongated cross-sectional shape, as shown in FIG. 3A, elongated in a direction perpendicular to the direction of the spectral dispersion (indicated in FIG. 3A), or the direction of the light which passes therethrough. Its transverse dimension, or its width, is made equal to the inner diameter of the sample cell opening 45 (that is, about 1 mm) so as to ensure a good mutual cancellation characteristic of optical variations with the light passing through the sample cell opening 45. In order to increase the throughput, the longitudinal dimension of the reference opening 51 is much greater, say, about 6 mm. Numerals 53 and 55 indicate the light-receiving window and the light-emitting window, respectively, of the reference opening 51 through which another portion of the dispersed light made incident onto the flow cell 41 enters and leaves the reference opening 51.

The optical system described above is so arranged that the image of the rectangular slit 29 formed on the flow cell 41, as shown in FIG. 3A at 57, is oriented in the direction of elongation of the cross-sectional shape of the reference opening 51. Since the sample cell opening 45 and the reference opening 51 are arranged such that the latter is elongated towards the former, the rectangularly shaped image 57 can efficiently cover the light-receiving windows 47 and 53 of the both openings 45 and 51, as also shown in FIG. 3A.

Operations of the detector thus structured will be described next. Light from the $D_2$ lamp, or from the tungsten lamp 23 and passed through the filter 25, is directed to the mirror 27. The orientation of the mirror 27 is adjusted by the mirror driver 28 such that the light source is properly selected, and the reflected light from the selected light source is directed to the slit 29 to generate a beam with a rectangularly elongated cross-sectional shape. The light thus formed is directed to the grating 33 by means of the second mirror 31. The orientation of the grating 33 is adjusted by means of the grating driver 34 such that dispersed light by the grating 33 is reflected by the third mirror 35 to be made incident as a parallel beam onto the flow cell 41, passing through both its sample cell opening 45 and reference opening 51. The light beams which have passed through these two openings 45 and 51 are both detected by the light-receiving device 39, and light absorbance by a sample is calculated from the results of the detection in a known manner.

It is to be noted that the throughput of light through the reference opening is increased according to this invention because the reference opening according to this invention is elongated in a direction perpendicular to that of the spectral dispersion. This has the effect of reducing the noise in absorbance caused by the reference opening, and this in turn has the effect of reducing the overall noise of the detector as a whole and improving its S/N ratio. Since the throughput of the reference opening is increased without adversely affecting the monochromatic characteristic of the light passing through the sample cell opening and the reference opening, the property of these openings to mutually canceling variations in light beams passing therethrough is not adversely affected.

Although the invention was described above by way of only one example, many variations and modifications are possible within the scope of this invention. For example, although the sample cell and reference cell openings are arranged vertically one above the other according to the described embodiment, they may be arranged next to each other, with the optical system suitably rearranged such that the dispersed light will form an image over an area covering their differently arranged light-receiving windows.

What is claimed is:

1. An ultraviolet and visible light absorbance detector comprising:

a flow cell having a sample cell opening and a reference opening formed therethrough extending parallel to each other in a longitudinal direction, said sample cell opening and said reference opening each having a light-receiving window, said reference opening having a cross-sectional shape which is elongated in a direction perpendicular to said longitudinal direction;

an optical system for forming an image of a slit with dispersed light over an area covering the light-receiving windows of both said sample cell opening and said reference opening and thereby also causing said dispersed light to pass through said sample cell opening and said reference opening; and a light-receiving device for detecting light which has passed through said sample cell opening and light which has passed through said reference opening each with a light-receiving element.

2. The detector of claim 1 wherein said sample cell opening has an inner diameter, said elongated cross-sectional shape of said reference opening has a width which is equal to said inner diameter of said sample cell opening.

3. The detector of claim 1 wherein said sample cell opening and said reference cell are separated in said perpendicular direction.

4. The detector of claim 1 wherein said sample cell opening is a part of a Z-shaped carrier liquid flow route formed through said flow cell.

5. The detector of claim 1 wherein said slit has a rectangular opening.

6. The detector of claim 1 wherein said optical system further includes a light source unit, a grating and mirrors for causing light emitted from said light source unit to pass through said slit and to be dispersed by said grating to generate said dispersed light and directing said dispersed light to said flow cell to pass through said sample cell opening and said reference opening.

7. The detector of claim 1 wherein said light source unit includes a $D_2$ lamp, a tungsten lamp and a rotatable mirror for selectively directing light from either said $D_2$ lamp or said tungsten lamp to said slit.

8. The detector of claim 1 wherein said image of said slit is rectangular.

9. A flow cell for a light absorbance detector, said flow cell comprising a block having a sample cell opening and a reference opening formed therethrough extending parallel to each other in a longitudinal direction, said sample cell opening and said reference opening each having a light-receiving window, said reference opening having a cross-sectional shape which is elongated in a direction perpendicular to said longitudinal direction.

10. The flow cell of claim 9 wherein said sample cell opening has an inner diameter, said elongated cross-sectional shape of said reference opening has a width which is equal to said inner diameter of said sample cell opening.

11. The flow cell of claim 9 wherein said sample cell opening and said reference cell are separated in said perpendicular direction.

12. The flow cell of claim 9 wherein said sample cell opening is a part of a Z-shaped carrier liquid flow route formed through said block.

* * * * *